(12) United States Patent
Kinoshita

(10) Patent No.: US 8,901,494 B2
(45) Date of Patent: Dec. 2, 2014

(54) SAMPLE ANALYZER

(71) Applicant: JEOL Ltd., Tokyo (JP)

(72) Inventor: Shingo Kinoshita, Tokyo (JP)

(73) Assignee: JEOL Ltd., Tokyo (JP)

( * ) Notice: Subject to any disclaimer, the term of this patent is extended or adjusted under 35 U.S.C. 154(b) by 0 days.

(21) Appl. No.: 14/036,291

(22) Filed: Sep. 25, 2013

(65) Prior Publication Data

US 2014/0091216 A1 Apr. 3, 2014

(30) Foreign Application Priority Data

Oct. 2, 2012 (JP) ................................. 2012-220107

(51) Int. Cl.
  *H01J 37/28* (2006.01)
(52) U.S. Cl.
  USPC ........... 250/310; 250/305; 250/306; 250/307; 250/309; 250/311; 250/492.1; 250/492.3; 702/22; 702/23; 702/27; 702/28
(58) Field of Classification Search
  USPC ................. 250/305, 306, 307, 309, 310, 311, 250/492.1, 492.3; 702/22, 23, 27, 28
  See application file for complete search history.

(56) References Cited

U.S. PATENT DOCUMENTS

| 4,453,226 A * | 6/1984 | Hobbs et al. ..................... 702/29 |
| 2007/0242269 A1* | 10/2007 | Trainer ......................... 356/336 |
| 2012/0181425 A1* | 7/2012 | Oohashi ........................ 250/307 |

FOREIGN PATENT DOCUMENTS

JP 2006125952 A 5/2006

\* cited by examiner

*Primary Examiner* — Nicole Ippolito

(74) *Attorney, Agent, or Firm* — The Webb Law Firm

(57) ABSTRACT

A sample analyzer is offered which creates a ternary scatter diagram representing a concentration ratio distribution of three elements out of several elements to be analyzed. This three-dimensional graph is created by adding an axis to the ternary scatter diagram and representing concentration information about the two additional elements on the added axis. The sample analyzer performs elemental analysis of a sample by scanning a primary beam over the sample and detecting a signal emanating from the sample. The added axis intersects the plane of the ternary scatter diagram.

6 Claims, 4 Drawing Sheets

SAMPLE ANALYZER

BACKGROUND OF THE INVENTION

1. Field of the Invention

The present invention relates to a sample analyzer which performs elemental analysis of a sample by irradiating the sample with a primary beam such as an electron beam and detecting a signal emanating from the sample such as characteristic X-rays.

2. Description of Related Art

A sample analyzer such as an electron probe microanalyzer (EPMA) can perform compositional analysis (elemental analysis) of elements present on the surface of a sample by irradiating the sample with an electron beam (primary beam) and detecting characteristic X-rays emanating from the sample.

In this case, a two-dimensional analysis of elements constituting the sample (measurement of a two-dimensional distribution) can also be performed by scanning the electron beam over the sample.

In this two-dimensional analysis, a concentration map of each element to be analyzed can be obtained based on a previously found relationship between the detected intensity of characteristic X-rays and mass concentration. Furthermore, a phase analysis for identifying compounds contained in the sample can be performed by finding the distributions of concentration ratios of the elements.

Where three elements are specified from several elements to be analyzed, the distributions of concentration ratios of the three elements can be represented as a ternary scatter diagram by plotting data in a graph based on obtained data about concentration distributions of the elements. Information plotted in this ternary scatter diagram permits identification of compounds contained in the sample.

One example of such a ternary scatter diagram is shown in FIG. 6 of JPA-2006-125952.

In the ternary scatter diagram based on the conventional technology, only concentration distributions of specified three elements can be represented.

In order to obtain more detailed information about the sample, it may be desired to refer to concentration information about elements other than the specified three elements, in addition to concentration information about the three elements.

SUMMARY OF THE INVENTION

In view of the foregoing, the present invention has been made. It is an object of the present invention to provide a sample analyzer capable of providing one three-dimensional graph to permit one to grasp the relationship of concentration distributions among three elements to concentrations of two additional elements by drawing a ternary scatter diagram indicative of the concentration ratio distributions of the three elements, adding a further axis to the ternary scatter diagram, and representing concentration information about the two additional elements on the added axis.

A sample analyzer according to the present invention is adapted to perform elemental analysis of a sample by scanning a primary beam over the sample and detecting a signal emanating from the sample in response to the scanning. A ternary scatter diagram is drawn based on concentration information about three elements out of several elements to be analyzed. The sample analyzer has means for creating a three-dimensional graph by adding a further axis intersecting the plane of the ternary scatter diagram and representing concentration information about two additional elements on the added axis.

In the present invention, a ternary scatter diagram is drawn based on concentration information about three elements out of several elements to be analyzed. A further axis intersecting the plane of the ternary scatter diagram is added, and concentration information about two additional elements is represented on the added axis, thus creating a three-dimensional graph.

Therefore, an operator who performs analyses can visually grasp the relation of concentration information about the three elements to concentration information about the two additional elements by visually checking the single three-dimensional graph. Hence, information useful for analysis of the sample can be quickly obtained.

DESCRIPTION OF THE INVENTION

A sample analyzer according to the present invention is hereinafter described with reference to the drawings.

Figures 1, 2:
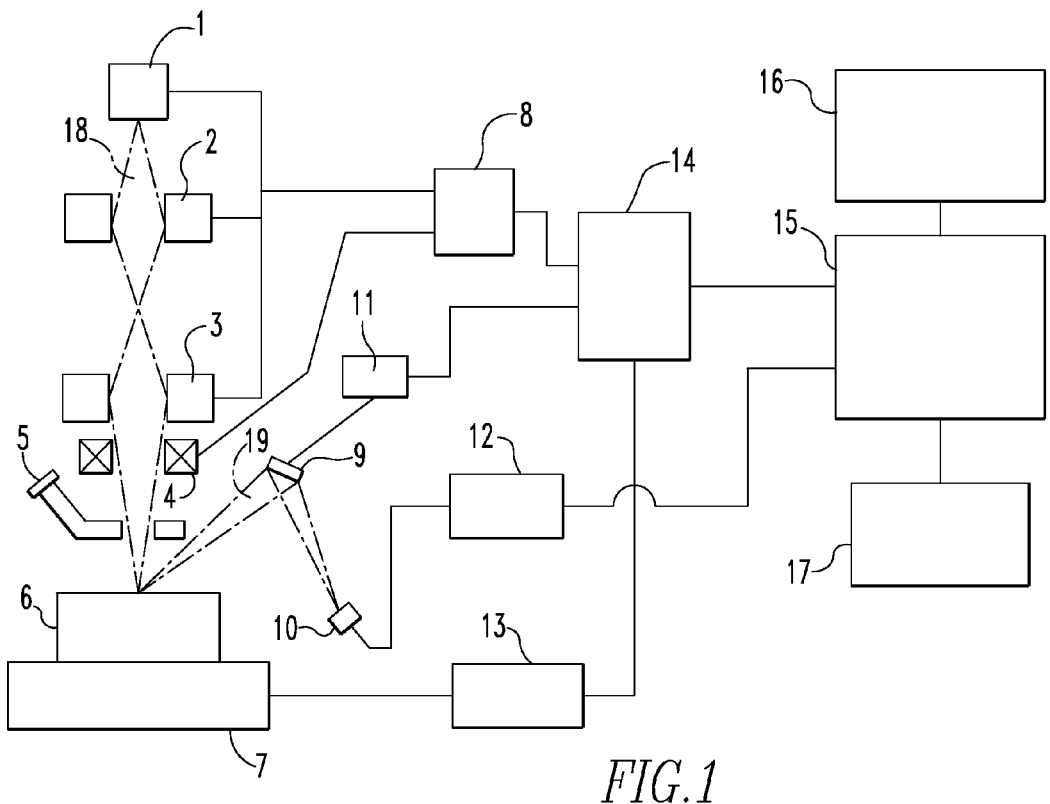
FIG. 1 is a schematic block diagram of a sample analyzer according to the present invention.
FIG. 2 is a diagram illustrating an Element Selection window permitting one to specify elements to be analyzed.

FIG. 1 schematically shows the structure of the sample analyzer according to the present invention. This analyzer has configurations of an electron probe microanalyzer.

The sample analyzer has an electron gun 1 that is an electron source. The gun 1 emits an electron beam 18 that is focused as an electron probe onto a sample 6 by a condenser lens or lenses 2 and an objective lens 3. In response to the electron beam irradiation, characteristic X-rays 19 corresponding to elements constituting the surface of the sample are emitted from the sample 6. The characteristic X-rays 19 are spectrally dispersed by a dispersive device 9 and detected by an X-ray detector 10. In order to perform a two-dimensional analysis of the sample 6, the focused electron beam 18 is scanned in two dimensions over the sample 6 by the deflecting action of an electron beam deflector 4.

The positions of the focused electron beam 18 on the sample 6, the dispersive device 9, and the X-ray detector 10 are kept located on a Rowland circle. The dispersive device 9 is controllably moved by a dispersive device controller 11 into a position where optical dispersion occurs (hereinafter may be referred to as a dispersion position) according to an element to be analyzed. Consequently, the characteristic X-rays 19 are spectrally separated by the dispersive device 9 at the dispersion positions corresponding to the elements to be analyzed.

An X-ray signal detected by the X-ray detector 10 at each dispersion position is processed in a given manner by an X-ray signal processor 12 and then sent to an arithmetic and control unit 15.

A two-dimensional analysis of the surface of the sample 6 can be performed about elements to be analyzed by holding the dispersive device 9 at each dispersion position and scanning the focused electron beam 18 over the sample 6 in two dimensions as described previously. The two-dimensional scanning of the sample 6 by the focused beam 18 may also be done by holding the beam position on the sample and moving a sample stage 7 in two dimensions under this condition.

The arithmetic and control unit 15 (which may comprise a programmed general purpose digital computer) receives a processed X-ray signal from the X-ray signal processor 12 and generates data for two-dimensional analysis of each element to be analyzed based on a scan signal used for scanning of the focused electron beam 18 and on the X-ray signal. In particular, the arithmetic and control unit 15 creates concentration maps of the elements based on previously found relations of mass concentrations of the analyzed elements to X-ray intensities. Furthermore, the arithmetic and control unit 15 creates a three-dimensional graph (described later).

The electron optical system of the present instrument is composed of the electron gun 1, condenser lenses 2, objective lens 3, and electron beam deflector 4 all of which are connected with an electron optics controller 8. The controller 8 is connected with the arithmetic and control unit 15 via an interface 14. In consequence, the operation of the electron gun 1, condenser lenses 2, objective lens 3, and electron beam deflector 4 is controlled by the arithmetic and control unit 15 via the electron optics controller 8.

The dispersive device controller 11 controlling the operation of the dispersive device 9 and a sample stage controller 13 controlling the operation of the sample stage 7 are connected with the arithmetic and control unit 15 via the interface 14. The operation of the dispersive device 9 and the sample stage 7 is controlled by the arithmetic and control unit 15 via the dispersive device controller 11 and the sample stage controller 13, respectively.

A display device 16 and input devices 17 are connected with the arithmetic and control unit 15. The display device 16 has a display unit such as a liquid crystal display, and displays analysis results obtained by the present invention. The input devices 17 include a keyboard or other key entry device and a pointing device such as a mouse. The input devices 17 permit an operator of the present instrument to perform input operations on the arithmetic and control unit 15. Indicated by reference numeral 5 is an optical microscope.

The sample analyzer according to the present invention is configured as described so far. The operation of the analyzer is next described.

The sample analyzer according to the present invention creates a three-dimensional graph indicative of not only concentration information about three elements of the sample 6 but also concentration information about two additional elements of the sample 6. Therefore, five or more elements in total are specified as elements to be analyzed by the operator.

In the present embodiment, for the sake of simplicity of illustration, it is assumed that five elements are specified as subjects of analysis by the operator. A specific example is given, in which the sample 6 consists of peridotite containing peridot [$(Mg(1-X)FeX)2SiO_4$]. Aluminum (Al), silicon (Si), potassium (Ca), iron (Fe), and magnesium (Mg), i.e., five elements, are specified as elements to be analyzed. Aluminum, silicon, and potassium correspond to the aforementioned three elements to be analyzed, while iron and magnesium correspond to the above-described two additional elements.

First, as shown in FIG. 2, an Element Selection window permitting one to select elements to be analyzed is displayed on the display device 16. Five elements, from element A to element E, can be specified on the Element Selection window. The elements A, B and C correspond to the aforementioned three elements, whereas elements D and E correspond to the aforementioned two additional elements. In the present analysis of the sample, a phase analysis of the sample 6 can be performed.

The operator manipulates the input devices 17 to enter the element symbols of aluminum, silicon, potassium, iron, and magnesium as elements A, B, C, D, and E, respectively, into their respective entry fields. Thus, five elements to be analyzed are specified.

The operator then manipulates the input devices 17 to give an instruction for starting execution of an analysis using the analyzer.

In response to the instruction, the analyzer carries out analysis of concentrations of the elements of the sample 6. In the analyzer, the dispersive device 9 is moved into successive analysis positions corresponding to the elements under control of the arithmetic and control unit 15. At this time, the dispersive device 9 is halted at each analysis position.

Under the condition where the dispersive device 9 is located at any one of the analysis positions, the focused electron beam 18 is scanned over the sample 6. In response to this, characteristic X-rays 19 are produced from the sample 6, spectrally separated by the dispersive device 9, and detected by the X-ray detector 10. An X-ray signal from the X-ray detector 10 is sent to the arithmetic and control unit 15 by way of the X-ray signal processor 12.

The arithmetic and control unit 15 creates data for two-dimensional analysis of each element at respective analysis position based on the scanning signal used when the focused electron beam 18 is scanned and on the X-ray signal. That is, the arithmetic and control unit 15 obtains concentration data about the elements at each measurement point within the scanned area based on previously found relationships of mass concentrations of the elements to X-ray intensities. Consequently, concentration data at each measurement point is obtained about each of the elements A-E.

Furthermore, the arithmetic and control unit 15 calculates the concentration ratios of the elements to a total ternary system consisting of these three elements A-C at each measurement point. In addition, the arithmetic and control unit 15 computes the concentration ratios of the elements D and E to a total binary system consisting of these two elements at each measurement point.

Figure 3:
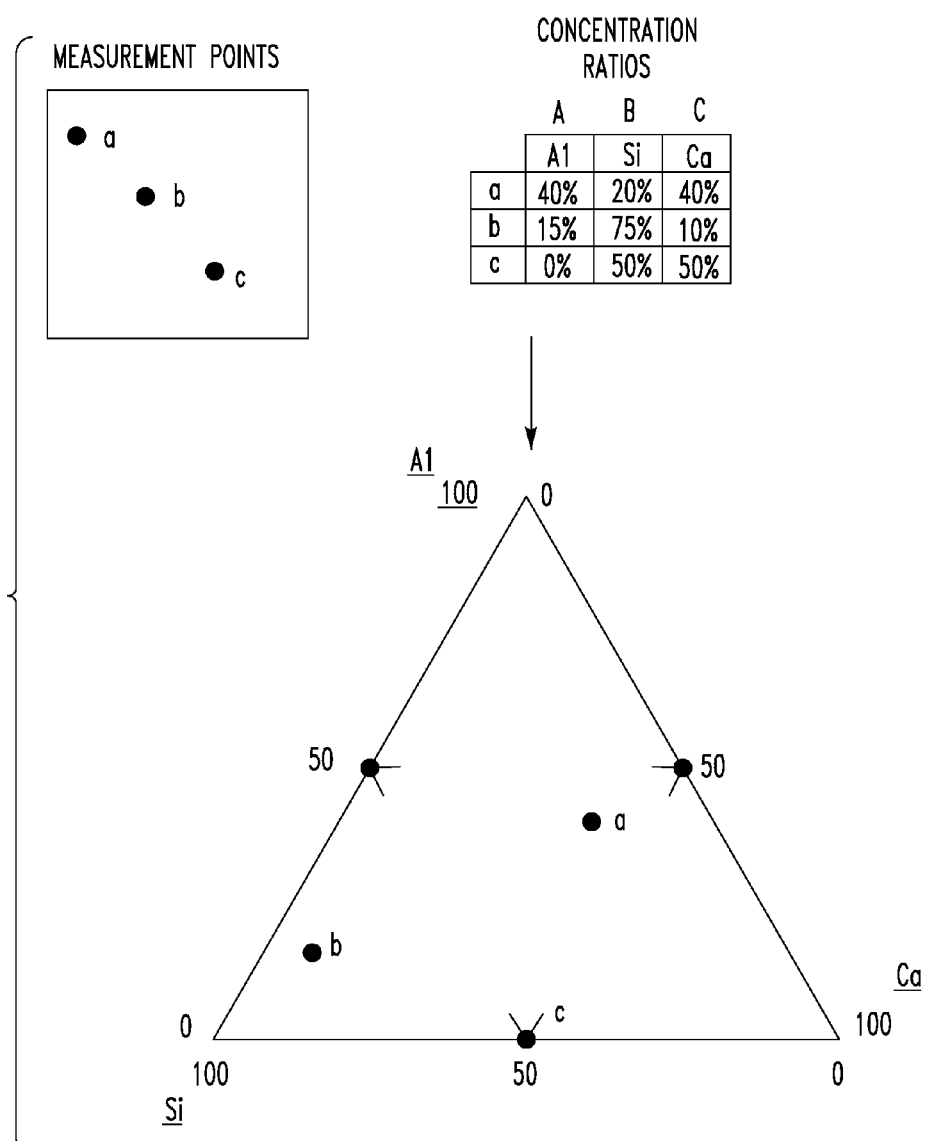
FIG. 3 illustrates a ternary scatter diagram obtained by elemental analysis.

An example of scatter diagram illustrating the concentration ratios of the three elements is shown in FIG. 3. In the example of FIG. 3, given three measurement points a, b, and c at which measurement data are collected are extracted from the measurement points within the scanned area. The concentration ratios of elements A (Al), B (Si), and C (Ca) at these three measurement points are represented in the table of FIG. 3. The scatter diagram located at the bottom of FIG. 3 is a ternary scatter diagram obtained under this condition.

In the present invention, the arithmetic and control unit 15 creates the aforementioned three-dimensional graph by adding concentration information about two additional elements D and E to the ternary scatter diagram (FIG. 3) indicative of the concentration information about the three elements A-C.

Figure 4:
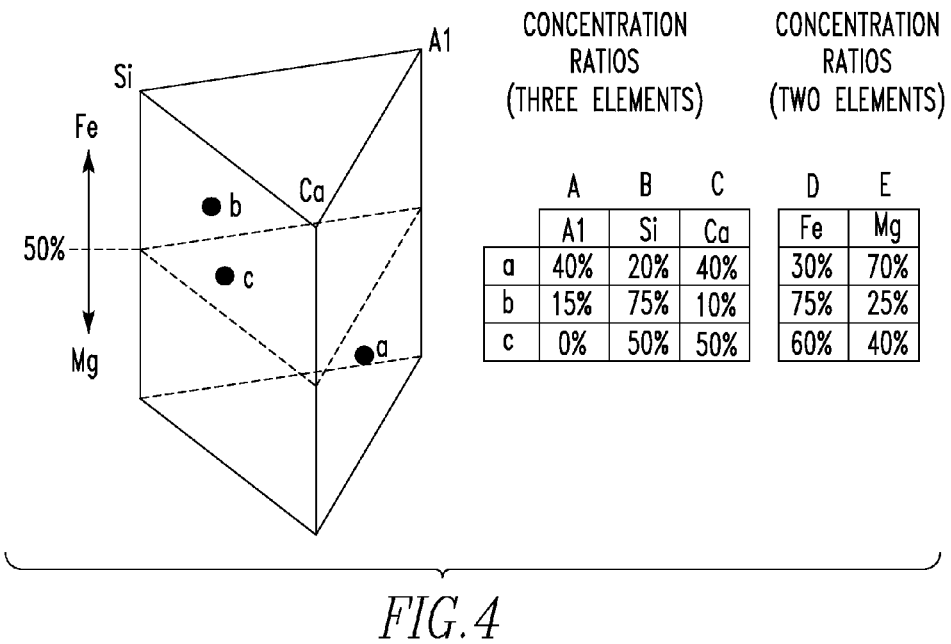
FIG. 4 illustrates a three-dimensional graph obtained by elemental analysis.

One example of the three-dimensional graph is shown in FIG. 4. This graph is based on the ternary scatter diagram consisting of a triangle whose apices are the elements A (Al), B (Si), and C (Ca), and is created by adding an axis perpendicular to the plane of the ternary scatter diagram, thus forming a three-dimensional space. The concentration information about the two elements D and E is represented on the added axis. That is, the concentration of the element D (Fe) increases with going upward along the added axis, and the concentration of the element E (Mg) increases with going downward along the added axis.

The three-dimensional graph is created by the arithmetic and control unit 15 and displayed by the display device 16.

In the three-dimensional graph of FIG. 4, the positions at which concentration distribution data obtained at the measurement points a, b, and c is plotted are indicated by black circles (●). The operator can see the concentration ratio between iron and magnesium at a glance as well as the concentration ratios about the three elements by visually checking the plotted points in the three-dimensional graph. Consequently, the operator can quickly see the information about the concentration ratios among the three elements. Additionally, the operator can quickly see how iron-rich regions or magnesium-rich regions of the sample are distributed in the Fe—Mg concentration ratio graph.

Where the sample 6 including the mineral (peridot [(Mg$_{(1-X)}$Fe$_X$)$_2$SiO$_4$]) is a subject of analysis as in the present embodiment, it is possible to afford a clue to the understanding of the process and conditions by which the mineral was formed at what temperatures by specifying iron (Fe) and magnesium (Mg) as two additional elements and finding the ratio in concentration between these two elements.

As a modification of the present embodiment, the operator is capable of manipulating the three-dimensional graph created and displayed as described above so as to rotate the graph about a spatial coordinate axis and of displaying the obtained state.

Figure 5:
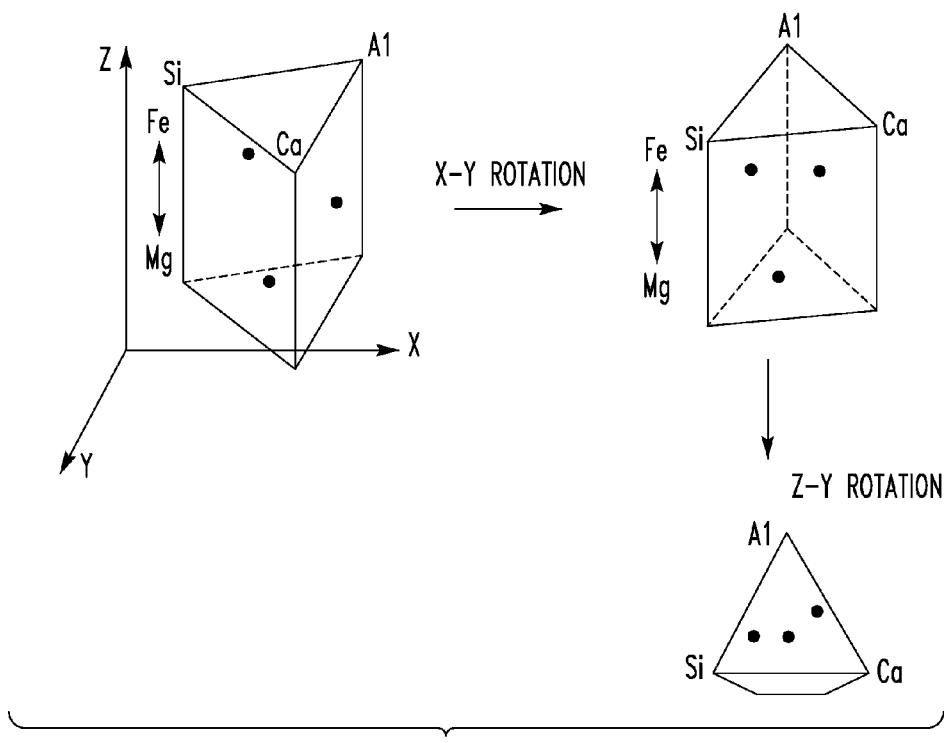
FIG. 5 illustrates modifications of the three-dimensional graph.
Figure 6:
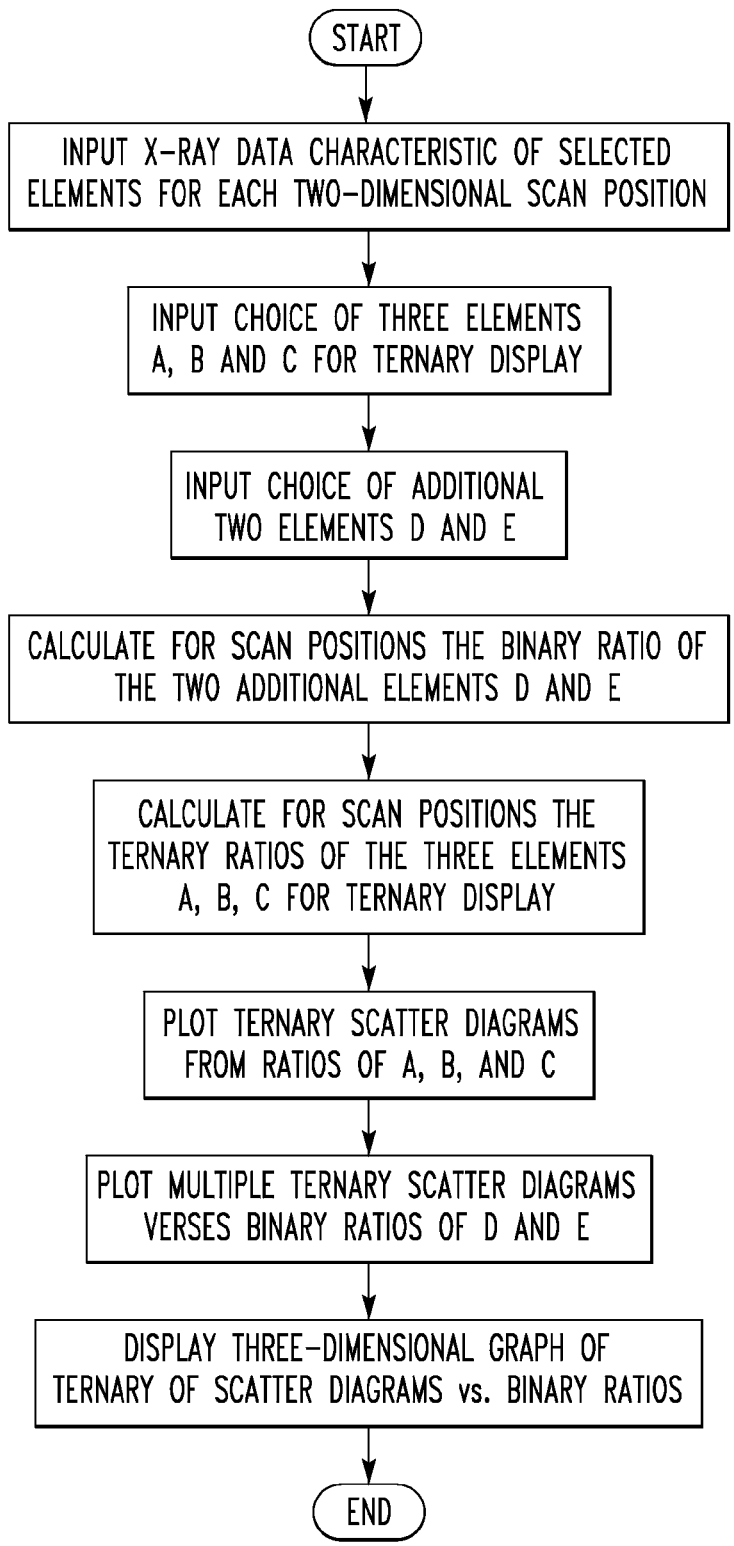
FIG. 6 illustrates a flow diagram of a program at least partially controlling the control unit to create a three-dimensional graph.

FIG. 5 shows one example of this. A three-dimensional graph shown in the left part of FIG. 5 can be displayed as a three-dimensional graph shown in the right part of FIG. 5 by rotating the left graph about an axis of rotation parallel to the Z-axis (i.e., within the X-Y plane).

Furthermore, the right three-dimensional graph can be displayed as a three-dimensional graph shown in the bottom of FIG. 5 by rotating the right graph about an axis of rotation parallel to the X-axis within the Z-Y plane.

In the description of the above-described embodiment, the axis added to the ternary scatter diagram is perpendicular to the plane of the scatter diagram. The invention is not restricted to this example. That is, the axis added to the ternary scatter diagram may intersect the plane of the scatter diagram at an arbitrary non-right angle.

In this way, the sample analyzer according to the present invention conducts elemental analysis of the sample 6 by scanning the primary beam (electron beam) 18 over the sample 6 and detecting signals (characteristic X-rays) 19 emanating from the sample 6. This instrument has the means (arithmetic and control unit) 15 for adding an axis intersecting the plane of a ternary scatter diagram created based on concentration information about three elements out of several elements to be analyzed and representing concentration information about two additional elements on the added axis, thus creating a three-dimensional graph. The added axis can be made perpendicular to the plane of the ternary scatter diagram.

Furthermore, the present sample analyzer has the display means (display device) 16 for displaying the three-dimensional graph. The displayed three-dimensional graph can be made rotatable about a spatial coordinate axis.

The present invention can also be applied to X-ray fluorescence spectroscopy. X-rays can be taken as the primary beam. Fluorescent X-rays emanating from the sample can be taken as a signal to be detected.

In the present invention, in elemental analysis of a sample containing multiple elements, it is possible to visually represent relations of concentration ratios of two additional elements to concentration ratios of three elements on one three-dimensional graph. Consequently, more useful information for identification of compounds included in the sample can be offered to the operator.

Having thus described my invention with the detail and particularity required by the Patent Laws, what is desired protected by Letters Patent is set forth in the following claims.

The invention claimed is:

1. A sample analyzer for performing elemental analysis of a sample by scanning a primary beam over the sample and detecting a signal emanating from the sample, said sample analyzer comprising:

means for creating a three-dimensional graph having a ternary scatter diagram created based on concentration information about three elements out of several elements to be analyzed, adding an axis intersecting a plane of the ternary scatter diagram, representing concentration information about two additional elements on the added axis.

2. The sample analyzer as set forth in claim 1, wherein said added axis is perpendicular to the plane of said ternary scatter diagram.

3. The sample analyzer as set forth in claim 1, wherein said primary beam is an electron beam, and wherein said signal is characteristic X-rays.

4. The sample analyzer as set forth in claim 1, wherein said primary beam is X-rays, and wherein said signal is fluorescent X-rays.

5. The sample analyzer as set forth in claim 1, further comprising display means for displaying said three-dimensional graph.

6. The sample analyzer as set forth in claim 5, wherein the three-dimensional graph displayed by said display means is rotatable about a spatial coordinate axis.

* * * * *